Figure 2:
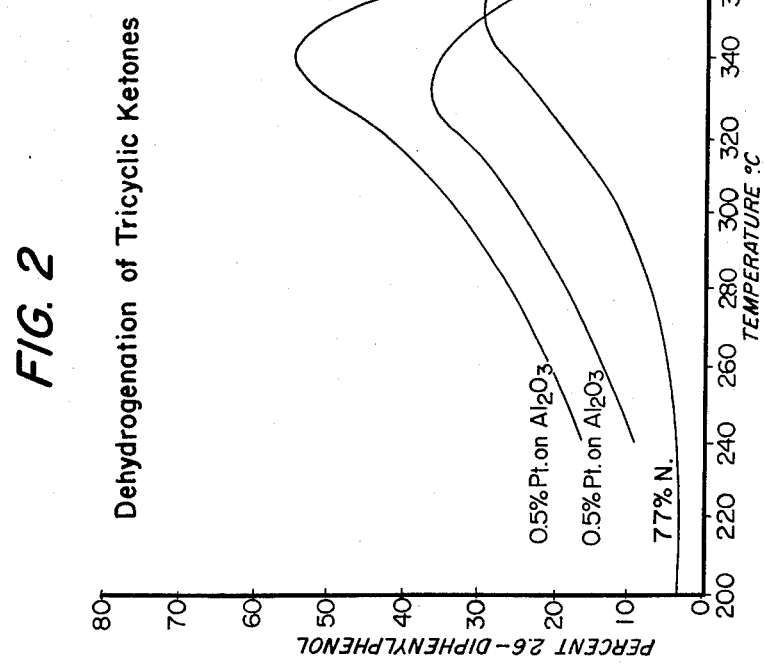

United States Patent [19]

Kapner et al.

[11] 3,972,951

[45] Aug. 3, 1976

[54] PROCESS FOR THE FORMATION OF 2,6-DIPHENYL-PHENOL

[75] Inventors: Robert S. Kapner, Loudonville, N.Y.; Donald L. Kippax, West Stockbridge, Mass.; Kevin E. Murphy; Lalitkumar H. Udani, both of Pittsfield, Mass.

[73] Assignee: General Electric Company, Pittsfield, Mass.

[22] Filed: Mar. 8, 1971

[21] Appl. No.: 122,078

Related U.S. Application Data

[63] Continuation of Ser. No. 601,771, Dec. 14, 1966, abandoned.

[52] U.S. Cl............................. 260/620; 260/586 C
[51] Int. Cl.$^2$........................................ C07C 37/06
[58] Field of Search....................... 260/620, 586 R

[56] References Cited
OTHER PUBLICATIONS

Plesek, "Collection Czech. Chem. Communications," vol. 21, pp. 375–381, 1956.

Primary Examiner—Norman Morgenstern
Attorney, Agent, or Firm—William F. Mufatti; Edward A. Hedman

[57] ABSTRACT

A process for the formation of 2,6-diphenylphenol involving the autocondensation of cyclohexanone with itself to form a mixture of cyclic ketones containing a tricyclic ketone fraction and the dehydrogenation of the tricyclic ketone fraction to form 2,6-diphenylphenol. The process is characterized by reaction conditions permitting the formation of 2,6-diphenylphenol on a commercial scale that is free of impurities and suitable for many new applications requiring high purity as synthesis of drugs, plastics and the like.

6 Claims, 3 Drawing Figures

PROCESS FOR THE FORMATION OF 2,6-DIPHENYL-PHENOL

This application is a continuation of application Ser. No. 601,771, filed Dec. 14, 1966, now abandoned.

This invention relates to a process for the formation of 2,6-diphenylphenol based upon the autocondensation of cyclohexanone.

The chemical, 2,6-diphenylphenol is an important material in the manufacture of dyes, drugs, plastics, insulating materials, insecticides and the like. However, insofar as it is known, there is currently no economical process for the manufacture of this material. One reason for this is the difficulty in selectively substituting aryl substituents in phenol in a position ortho to the —OH group.

General methods for the preparation of substituted phenols comprise contacting phenol with an unsaturated aromatic hydrocarbon halide or alcohol in the presence of a condensing catalyst such as sulfuric acid, siliceous materials, or catalysts of the Friedel Crafts type such as anhydrous aluminum chloride. Methods of this nature generally result in a mixture of phenols containing unreacted phenol, monosubstituted phenols and mixtures of disubstituted phenols such as 2,6-disubstituted phenol and 2,4-disubstituted phenol. The 2,6-disubstituted phenol cannot readily be separated from the remaining components in the mixture economically because the melting points of the disubstituted materials are very close to each other. In addition, the yield of the 2,6-disubstituted phenol is low.

In U.S. Pat. No. 2,804,481 issued Aug. 27, 1962, a method for the formation of dicyclohexyl alkyl phenols is disclosed. This method comprises mixing or blending cyclohexene or a material capable of yielding cyclohexene with an alkyl phenol. The reaction is carried out in the presence of an acid condensation catalyst such as sulfuric acid, hydrochloric acid, phosphoric acid, zinc chloride, etc. The product is a 2,6-dicyclohexyl-4-alkyl phenol. A material of this nature could be dehydrogenated to form the corresponding 2,6-diphenyl-4-alkyl phenol. The difficulty with this reaction is that an alkyl radical must be substituted in the 4 position of the phenol, thus yielding an alkyl substituted diphenyl-phenol. In addition, the process is expensive because both phenol and cyclohexene are necessary raw materials.

It has now been found in accordance with the present invention that the disadvantages of the prior art procedures above described can be substantially overcome by a process which utilizes cyclohexanone as a starting material rather than phenol. The process comprises the autocondensation of cyclohexanone to form a mixture of tricyclic ketones which can be dehydrogenated to form 2,6-diphenylphenol economically and in high yields.

It is, therefore, an object of this invention to provide a process for the formation of 2,6-diphenylphenol wherein the phenyl radicals are substituted substantially exclusively in a position ortho to the —OH of the phenol. It is also an object of this invention to provide a process for forming 2,6-diphenylphenol by a process comprising the autocondensation of cyclohexanone in the presence of an alkaline catalyst to form a mixture of tricyclic ketones that are dehydrogenated to yield 2,6-diphenylphenol. Other objects and advantages of this invention will be in part apparent and in part disclosed in the description which follows.

Figure 1:
Figure 3:
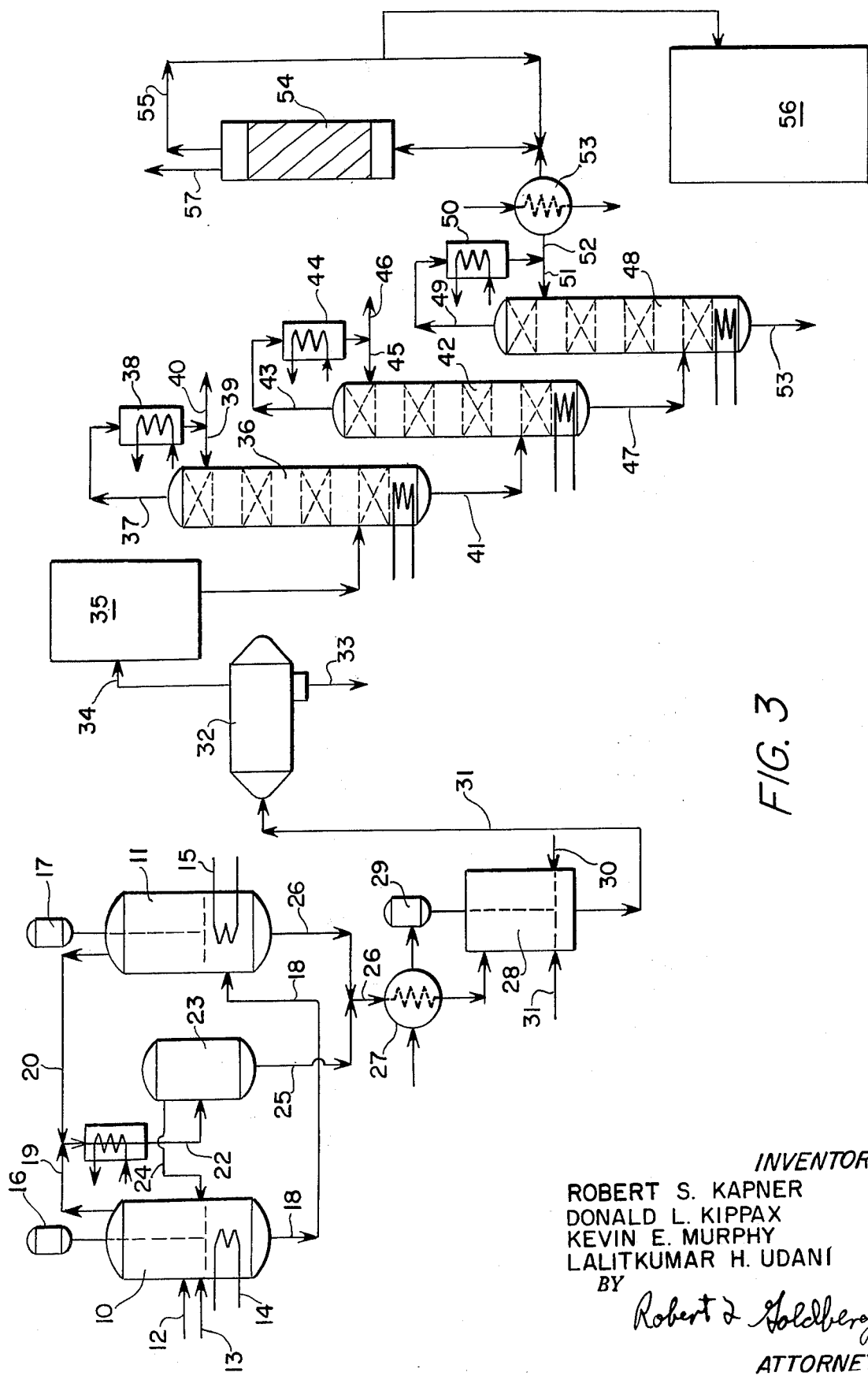

In the drawings:

FIG. 1 graphically represents the autocondensation of cyclohexanone to its reaction products;

FIG. 2 graphically represents the dehydrogenation of a mixture of tricyclic ketones in the presence of selected dehydrogenation catalysts; and FIG. 3 is a schematic drawing showing principle apparatus components for the formation of 2,6-diphenylphenol in a preferred operative relationship.

The autocondensation of cyclohexanone is a modified base catalyzed aldol condensation reaction accompanied by the liberation of water. The desired products resulting from the reaction are tricyclic ketones corresponding to the following formulas:

1) 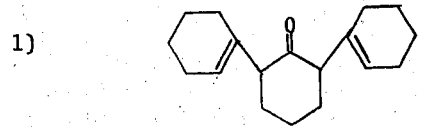

2) 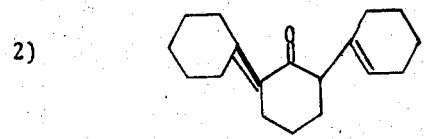

3) 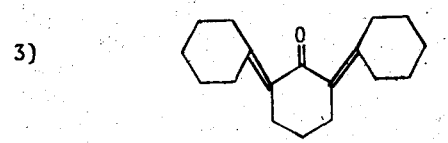

For brevity, these materials will be referred to as the "tricyclic ketones" throughout the remainder of this specification.

Monosubstituted cyclohexanones are also formed during the autocondensation reaction. For brevity, these materials will be referred to as "bicyclic ketones" throughout the remainder of this specification.

In addition, high boiling materials are formed when the autocondensation reaction is carried out at high temperatures. Typical of these materials are m-terphenyl, triphenylene, chrysene, etc. For brevity, all of these materials will be hereinafter referred to as "high boilers".

Care must be exercised in performing the auto-condensation reaction to avoid the formation of undesirable by-products. For example, if the reaction conditions used are too mild, there is insufficient conversion of the cyclohexanone to the tricyclic ketones. In addition, large quantities of partially reacted bicyclic ketones are found in the product mixture. On the other hand, if severe reaction conditions are used, undesirable high boilers are formed. These materials are difficult to separate from the product and result in discolored diphenylphenols. In addition, the high boilers represent yield losses and resulting higher costs.

FIG. 1 represents graphically the conversion of cyclohexanone to its condensation products. The conversion was carried out in a batch process at a temperature of 175°C. in the presence of a 50% aqueous sodium hydroxide solution wherein the sodium hydroxide concentration amounted to 1 mole per 50 moles of cyclohexanone feed. The conversion of the cyclohexanone feed is represented by Curve A. Conversion to oxidation products during the first hour of reaction is rapid. Curve B illustrates the formation of the tricyclic ketones represented by formulas (1), (2) and (3) above. The conversion to the tricyclic ketones levels off after the first few hours of the reaction. The formation of the intermediate condensation products are represented by Curve C. These products are primarily bicyclic ketones. They may be separated from the tricyclic ketones along with the unreacted cyclohexanone and recycled as feed in a manner to be described more fully below. Curve D represents the formation of high boiling components. The slope of Curve D has been exaggerated for purposes of illustration. At 175°C., the high boiling components normally constitute less than 1.0% by weight of the product.

The autocondensation reaction can be performed at temperatures below 150°C., however, 150°C. constitutes a practical minimum. At lower temperatures, the conversion of the cyclohexanone to tricyclic ketones takes place too slowly and there is insufficient conversion to make the process economical. A practical maximum temperature for purposes of the present invention is 200°C. If the temperature exceeds 200°C., the quantity of high boilers in the reaction product becomes intolerably large resulting in large yield losses. For example, a condensation reaction performed at a temperature of 250°C. results in a product having in excess of 25% by weight high boilers. The quantity of tricyclic ketones in the product did not exceed 40% even though the high temperature was used. This is probably due to the conversion of the tricyclic ketones to high boilers.

A temperature range of 170° to 190°C. constitutes a preferred temperature range for purposes of the present invention because autocondensation reactions performed within this range result in conversions with the highest yields of tricyclic ketones with acceptably low yields of high boilers.

A reaction time of from ½ to 3 hours is acceptable for a reaction temperature of 150° to 200°C. A reaction time in excess of 3 hours is undesirable as the conversion ratio levels off after about 2 to 2½ hours. A reaction time less than ½ hour is undesirable because of insufficient conversion of the cyclohexanone to tricyclic ketones.

It should be understood that the reaction temperature and duration is, to some extent, dependent upon the system parameters. The product stream should contain from 20 to 70% by weight tricyclic ketones and preferably from 30 to 45% tricyclic ketones. Accordingly, the reaction conditions should be regulated to meet this requirement.

Any strong base may be used as a catalyst for the autocondensation reaction. The base should preferably be soluble in the reaction mixture, and is desirably added in the form of an aqueous solution. It has been found that heterogeneous catalysts result in low conversion yields. The catalyst concentration may very between 0.1 to 5 mole % of the cyclohexanone feed. A preferred catalyst is either an aqueous solution of sodium hydroxide or potassium hydroxide.

The tricyclic ketones represented by formula (1), (2) and (3) above are separated from the remainder of the condensation reaction product. Any means known to those skilled in the art may be used, however. distillation has been found to be the most convenient. The unreacted cyclohexanone and partially reacted bicyclic ketones can be recovered and saved for a later condensation reaction, or in a continuous process, they may be continuously recycled as feed to an autocondensation reactor.

The tricyclic ketones formed by the autocondensation of cyclohexanone are readily dehydrogenated to form the desired 2,6-diphenylphenol. It is unique to the present invention that all three tricyclic ketones can be simultaneously dehydrogenated to yield 2,6-diphenylphenol. In other words, there is no need to separate the three ketones from each other and individually treat them. The dehydrogenation reaction may be carried out in either a fixed bed or slurry type reactor. Any of the well known dehydrogenation catalysts known in the art may be used. Typical catalysts include, but are not limited to, platinum on silica, platinum on carbon, platinum on charcoal, platinum on alumina, platinum on metal carbonate, palladium on alumina, palladium on carbon, nickel on kieselguhr, nickel on alumina, rhodium on alumina, rhodium on carbon, etc. Of these catalysts, those containing platinum or palladium on a substrate are preferred.

The conversion of the tricyclic ketones to the diphenylphenol appears to occur through a sequence of steps, each reaction product in the sequence differing from those alongside it with respect to its state of reduction. It is believed that the tricyclic ketones represented by formulas, (1), (2) and (3) above are converted to 2,6-diphenylphenol in the following manner.

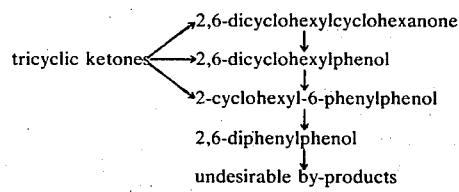

From a process standpoint, it is very difficult to regulate the reaction conditions so that a product consisting essentially of 2,6-diphenylphenol is obtained. In practice, yields of up to 95% by weight of the phenol are recovered with the remaining product consisting of the above noted intermediate dehydrogenation materials. These intermediates can be removed from the product stream and recycled to the dehydrogenation reactor.

The temperatures at which the dehydrogenation reaction is performed is determinative of the composition of the final product. FIG. 2 graphically represents the dehydrogenation of a mixture of tricyclic ketones as a function of temperatures for three different catalysts. As the temperature increases from 240°C., the amount of 2,6-diphenylphenol increases. However, this is accompanied by appearance of undesirable by-products such as m-terphenyl and α-phenyldibenzofuran. The formation of the by-products impairs the process economy because it is at the expense of other desirable materials. The largest conversion to 2,6-diphenylphenol takes place within a temperature range of 300° to 350°C., and this constitutes a preferred temperature range for purposes of the present invention. Above 360°C., the character of the reaction changes markedly. When the feed material is composed of a mixture of tricyclic ketones, the diphenylphenol content decreases rapidly and the tricyclic ketones reappear in the product. The reappearance of this material is at the expense of the diphenylphenol. The other components in the reaction product remain substantially constant.

This may be due to vaporization of the tricyclic ketones at the elevated temperatures.

The time of contact between the tricyclic ketones and the dehydrogenation catalyst is not critical. Five minutes is sufficient. Extension of this time up to an hour does not result in a significant change in the product composition.

A preferred embodiment of this invention will now be described in greater detail with reference to FIG. 3 of the drawings which is a schematic showing principal apparatus components in operative relationship. It should be understood that the drawing represents a continuous process, but the process may be operated as a batch process, a continuous process or a mixture of both batch and continuous wherein portions of the operation are performed continuously and portions are performed on a batch basis.

With reference to FIG. 3 of the drawings in greater detail, the numerals 10 and 11 indicate successive reactors wherein the autocondensation reaction takes place. Reactor 10 is connected with two conduits at a point slightly below its midsection. A feed of cyclohexanone and, if desired, recycle bicyclic ketones and unreacted cyclohexanone flow into reactor 10 through conduit 12 and a solution of an alkaline catalyst enters reactor 10 through conduit 13. Reactors 10 and 11 are equipped with heating coils 14 and 15 and agitators 16 and 17, respectively. The autocondensation reaction of the cyclohexanone is designed to take place under moderate conditions in successive stages to eliminate to a large extent, the formation of undesirable by-products. For purposes of illustration, two reactors (10 and 11) are illustrated. It should be understood, however, that a plurality of reactors may be used in series to effect the conversion of the cyclohexanone to the desired product. In practice, it has been found that successive cascade reactors greatly increase the efficiency of the reaction.

The autocondensation reaction of the cyclohexanone is initiated in reactor 10 by the introduction of cyclohexanone and an alkaline catalyst solution. The alkaline catalyst solution may vary from a 20 weight % aqueous solution to a saturated solution of either sodium hydroxide or potassium hydroxide. The reaction is performed preferably under atmospheric pressure though it may be performed under partial vacuum. Pressures exceeding atmospheric are, in general, undesirable. Reaction temperature at atmospheric pressure may vary between 150°C. and 200°C. though the preferred temperature ranges between 170°C. and 190°C.

Within reactor 10, the cyclohexanone is partially condensed and the crude product which consists of bicyclic ketones, tricyclic ketones, unreacted cyclohexanone, alkaline solution, and minor quantities of high boilers passes out of the bottom of reactor 10, through conduit 18, and into the bottom of reactor 11 where the condensation reaction continues. The reaction temperature in reactor 11 may be maintained at a somewhat higher level than that used in reactor 10 and preferably, at the boiling point of the reaction mixture. The boiling point of the reaction mixture in reactor 11 is somewhat higher than that of reactor 10 because some volatiles are converted during the course of the reaction. Residence time in both reactors may vary between 30 and 180 minutes. The reaction products are withdrawn when a maximum of 70% and preferably 45% or less of the feed is converted to the tricyclic ketones.

The vapors above the reaction mixture in both reactors 10 and 11 are composed primarily of the water generated during the reaction and unreacted cyclohexanone. The vapors are passed from reactors 10 and 11 through conduits 19 and 20 respectively and liquified in condenser 21. The liquid mixture is passed through conduit 22 and into a decantation chamber 23. The mixture separates and forms two phases in the decanter. One phase is primarily cyclohexanone and the second phase primarily water. The cyclohexanone is removed from the top of the decanter 23 and recycled to reactor 10 through conduit 24. The recycling of the cyclohexanone serves two purposes. The first and more obvious purpose is to conserve cyclohexanone. Secondly, the recycling of the cyclohexanone allows the reaction to take place in the absence of a solvent. This is important as it is possible that the presence of a solvent would contribute to the formation of undesirable by-products and in addition, requires additional separation equipment. The water phase from decanter 23 may be discarded or passed to a neutralizer tank through conduit 25 if it is desired to recover the water soluble cyclohexanone content.

The effluent composition in reactor 11 at the controlled completion of the condensation contains a maximum of 70% tricyclic ketones, from 30 to 60% bicyclic ketones, about 5% unreacted cyclohexanone and about 5% alkali, water and high boilers, all by weight. The bicyclic ketones and unreacted cyclohexanone are separated and recycled to the condensation reactors in a manner described in more detail below. The effluent composition is removed from the bottom of reactor 11 and passed through conduit 26 and heat exchanger 27 wherein the effluent is cooled to about 60°C. It is then passed into neutralizer tank 28 equipped with agitator 29. The neutralizer tank has provision for introduction of an acid through conduit 30 and a lower aliphatic alcohol through conduit 31.

It is desirable that all of the alkali be removed from the organic layer in neutralizer tank 28. To successfully accomplish this, the organic layer is washed with large quantities of water, neutralized with a concentrated acid such as hydrochloric, and again washed with water. The organic layer should have a final pH of approximately 7.0. A lower aliphatic alcohol is added to the neutralizer tank 28 to aid in the separation of the water layer and the organic layer.

The neutralized organic phase and the resultant water phase are removed from the neutralizer tank 28 and passed through conduit 31 and into separator 32. The water phase is removed through conduit 33 and either disposed of or treated to recover minor quantities of methanol. The organic phase passes through conduit 34 and into storage tank 35. At this point, the organic phase contains methanol, bicyclic ketones and a mixture of tricyclic ketones.

The tricyclic ketones are isolated by passing the organic phase contained in storage tank 35 through three successive distillation columns. Methanol and water are removed as vapor from the first distillation column 36 through overhead conduit 37. The column is equipped with condensor 38 and has provision for reflux through conduit 39. The liquified methanol water mixture is removed through conduit 40 and passed to a storage tank (not shown) for recovery of methanol. The bottoms from column 36 are removed through conduit 41 and passed into distillation column 42, wherein the bicyclic ketones are removed as a vapor through conduit 43 and liquified in condensor 44. Again, provision is made for reflux through conduit 45. The recovered bicyclic ketones are passed through conduit 46 to a storage tank (not shown) wherein they are stored and used as feed material in subsequent autocondensation reactions.

The bottoms from tower 42 are passed through conduit 47 to distillation column 48. The desired product i.e., the tricyclic ketones are removed from column 48 as a vapor through conduit 49 and condensed in condensor 50. Provision is made for reflux through conduit 51 and the ketones are passed through conduit 52 for further processing. The bottoms from column 48 contain only small portions of high boilers which are removed through conduit 53.

All three of the above-described distillation operations are preferably performed under vacuum or in an inert atmosphere because it has been found that oxygen tends to decompose the ketones.

The next stage in the operation comprises the formation of 2,6-diphenylphenol by dehydrogenation of the tricyclic ketones. This is accomplished by passing the ketones over a dehydrogenation catalyst contained in a dehydrogenation reactor. A fixed bed reactor is preferred, but a slurry type reactor may be used. The mixture is passed through conduit 52 through heat exchanger 53 where the vapors are liquified, cooled and passed into the dehydrogenation reactor 54. Dehydrogenation has been carried out at temperatures in excess of 350°C., but for purposes of the present invention, a temperature ranging between 250° and 360°C., and preferably, between 300° and 350°C. is used. The residence time in the reactor preferably exceeds 5 minutes.

The product stream emerging from the dehydrogenation reactor contains 2,6-diphenylphenol as well as intermediate partially dehydrogenated materials. The product stream passes through conduit 55 and into storage tank 56. Hydrogen is evolved through conduit 57. A portion of the product stream can be recycled if desired. The 2,6-diphenylphenol can be separated from the remaining materials by any means known to those skilled in the art, such as, for example, by fractional distillation.

The foregoing has been with reference to a preferred embodiment of this invention, however, it should be understood that changes and modifications may be made within the scope of the invention. The invention will be better represented by the following examples wherein all percentages are by weight unless otherwise specified.

EXAMPLE 1

Approximately 1000 cc. of cyclohexanone were charged to a three neck flask equipped with a stirrer, condenser and Dean Stark trap. The flask was heated to approximately 150°C. When the reaction temperature was obtained, 0.178 moles of solid potassium hydroxide were rapidly added to the reaction mixture. This was taken as zero reaction time. Periodically, during the reaction period, 1–2 moles of the reacting mass were removed, rapidly cooled and analyzed. The following table sets forth the composition of the reaction mixture at various periods during the course of the reaction.

TABLE I

| Time (hrs.) | Cyclohexanone | PRODUCT COMPOSITION % | | |
| --- | --- | --- | --- | --- |
| | | bicyclic ketones | tricyclic ketones | high boilers |
| 0 | 100.0 | 0 | 0 | 0 |
| 0.50 | 72.0 | 28.0 | 0 | 0 |
| 1.25 | 38.9 | 54.8 | 6.3 | trace |
| 1.75 | 27.1 | 60.8 | 12.0 | " |
| 2.25 | 22.0 | 65.0 | 13.0 | " |
| 2.75 | 18.0 | 66.5 | 15.5 | " |
| 3.25 | 12.5 | 61.7 | 25.7 | " |

EXAMPLE 2–4

The procedure for Example 1 was repeated three times, but the reaction temperature for the following three runs was maintained at 182°C., 196°C. and 250°C., respectively. Table II summarizes the product compositions for these runs after 1.25 hours of operation.

TABLE II

| Temp. °C. | Cyclohexanone | PRODUCT COMPOSITION % | | |
| --- | --- | --- | --- | --- |
| | | bicyclic ketones | tricyclic ketones | high boilers |
| 182 | 26.6 | 50.3 | 26.1 | 1.4 |
| 196 | 19.7 | 45.3 | 33.1 | 2.4 |
| 250 | 0 | 58.6 | 15.2 | 26.2 |

EXAMPLE 5

Approximately 370 cc. of cyclohexanone and 630 cc. of bicyclic ketones were charged to a three neck flask equipped with a stirrer, condenser and Dean Stark trap. The flask was heated to approximately 168°C. When the reaction temperature was reached, approximately 0.21 moles of solid sodium hydroxide were rapidly added to the reaction mixture. This was taken as zero reaction time. Periodically, during the reaction period, 1–2 moles of the reacting mass were removed, rapidly cooled, and analyzed. The following table sets forth the composition of the reaction mixture at various periods during the course of the reaction.

TABLE III

| Time (hrs.) | Cyclohexanone | PRODUCT COMPOSITION % | | |
| --- | --- | --- | --- | --- |
| | | bicyclic ketones | tricyclic ketones | high boilers |
| 0 | 37.0 | 63.0 | 0 | 0 |
| 0.3 | 27.4 | 64.5 | 8.5 | 0 |
| 0.5 | 18.6 | 67.7 | 14.4 | 0 |
| 1.0 | 10.8 | 64.6 | 25.6 | 0 |
| 1.5 | 9.5 | 58.7 | 32.7 | 0 |
| 2.0 | 10.5 | 57.7 | 32.5 | 0 |
| 2.5 | 10.5 | 54.1 | 36.3 | 2 |
| 3.0 | 9.8 | 54.5 | 36.9 | 0 |

EXAMPLE 6

This example describes the dehydrogenation of a mixture of tricyclic ketones formed by the auto-condensation of cyclohexanone.

A continuously operating tubular reaction system was used for the dehydrogenation. The apparatus consisted of a heated storage vessel containing tricyclic ketones, a pumping system used to transfer liquid feed from storage to the reactor, and the reactor which was made from a length of stainless steel tubing containing the catalyst mass. The reaction tube and the catalyst were immersed in a bed of fine sand which was fluidized by electrically heated air. The reactor tube was in the form of a U, one leg of the U being connected above the sand bath to the feed line and the other leg to the effluent line. Catalyst was packed in the tube and contained by plugs of glass wool.

The tube was loaded with 1/8 inch diameter pellets of a catalyst consisting of 0.5% platinum on an alumina substrate. The reactor temperature was set at approximately 330°C., but it was found to vary between a temperature of 320° and 336°C. during the course of the run. The tricyclic ketones were passed through the reactor at an average flow rate of 0.34 cc/min. The space velocity through the catalyst bed was maintained at approximately 3.1 reciprocal hours. At the end of approximately 8 hours, a sample of the reactor effluent was taken and analyzed. It was found to contain 7.6% saturated tricyclic ketones, 9.3% unreacted feed, 36.5% partially dehydrogenated materials such as 2-cyclohexyl-6-phenylphenol and 2,6-dicyclohexylphenol, 42.2% 2,6-diphenylphenol and 1.3% α-phenyldibenzofuran.

EXAMPLE 7

A feed consisting of 50% cyclohexanone and 50% bicyclic ketone recycle was charged to a continuously agitated first reactor maintained at a temperature of 180°C. A 50% sodium hydroxide solution was continuously added in an amount equivalent to approximately 1 mole of sodium hydroxide per 5 moles of feed. The reaction mixture had a residence time in the reactor of approximately 3/4 hours. Vapors of water and a cyclohexanone azeotrope were continuously removed from the top of the reactor and condensed and separated into water and cyclohexanone layers. The latter was separated from the water and continuously recycled to the reactor. The reaction mixture was continuously passed to a second reactor maintained at a temperature of approximately 185°C. Residence time in the second reactor was approximately 3/4 hours. The water and cyclohexanone azeotropic vapors were continuously removed as generated, passed through a condenser and into a decanter where the cyclohexanone was removed and recycled to the first reactor. The effluent from the second reactor had a composition consisting of approximately 46.5% bicyclic ketones, 31.5% tricyclic ketones and 20% unreacted cyclohexanone and 2.0% water, alkali and high boilers. The reactor effluent was cooled to about 60°C. and passed to a neutralizer where it was washed with methanol and water, neutralized to a pH of 7.0 with concentrated hydrochloric acid and again washed with methanol and water. Approximately 1 lb. of methanol was used for every 40 lbs. of reaction mixture. Water was separated from the effluent and pumped to a storage tank. The crude material so formed was then distilled three times using packed columns. In the first distillation the reboiler was maintained at 101°C. and methanol and trace amounts of water were removed. The second distillation was conducted under vacuum of 20 millimeters of mercury and the temperature in the reboiler was maintained at approximately 200°C. The vapor phase consisted primarily of bicyclic ketones that were passed to a storage tank for further recycling to the condensation reactors. The third distillation was performed at a reboiler temperature of 250°C. under a vacuum of 20 millimeters of mercury. The tricyclic ketones were recovered as vapors from the top of the column. They were passed through a condenser and cooled to a temperature of 60°C. They were then passed to a dehydrogenation reactor to form 2,6-diphenylphenol. The catalyst used in the dehydrogenation reactor was approximately 0.5% palladium on alumina. The dehydrogenation temperature was maintained at approximately 295°C. The hold-up time in the dehydrogenation reactor was approximately 20 minutes. These conditions were sufficient to convert approximately 40% of the tricyclic ketone to 2,6-diphenylphenol.

EXAMPLE 8

The general procedure of Example 1 was repeated, however the feed was pure cyclohexanone. The temperature in the first reactor was maintained at approximately 200°C. and residence time was approximately 1.0 hour. The temperature in the second reactor was approximately 205°C. and residence time was approximately 1 hour. The reaction mixture leaving the first reactor contained approximately 10.2% unreacted cyclohexanone, 38.8% bicyclic ketones, 38.1% tricyclic ketones, 9.5% water and 3.6% high boilers. The reaction mixture leaving the second stage contained approximately 2.8% cyclohexanone, 39.3% bicyclic ketones, 52.3% tricyclic ketones, 1.2% water and 4.9% high boilers. A comparison of this example with the previous example indicates that the more severe reaction conditions i.e., the longer residence times in the reactor and the higher temperatures caused an increase in the concentration of high boilers. The remaining steps in the procedure were the same as those in Example 7.

It should, of course, be apparent to those skilled in the art that changes may be made in the particular embodiments of the invention described which are within the full intended scope of the invention as defined by the appended claims.

We claim:
1. In a process for the preparation of 2,6-diphenylphenol, the steps comprising:
    a. passing a reaction mixture consisting of an aqueous alkaline catalyst and a cyclic ketone selected from the group consisting of cyclohexanone and mixtures thereof with bicyclic condensation products of cyclohexanone successively through at least two condensation reactors in a condensation reactor zone wherein the reaction temperature is from 150° to 200°C.;
    b. removing said condensation product from said reactor zone when it contains a maximum of 70% of tricyclic ketones by weight;
    c. collecting and condensing the vapors above the condensation reactors in the reactor zone and passing the same to a decantor wherein a water phase and a cyclohexanone phase is formed;
    d. separating said cyclohexanone phase from the water phase and recycling said cyclohexanone phase to the first condensation reactor in said reaction zone whereby it acts as a source of cyclohexanone and as a solvent for the reaction mixture;
    e. cooling said condensation product as it leaves said reaction zone;
    f. passing said condensation product to a neutralizer and neutralizing by adding an acid to form an aqueous phase and an organic phase;
    g. separating said organic phase from said aqueous phase;
    h. passing said organic phase through a first distillation column to remove water, a second distillation column to remove bicyclic autocondensation products of cyclohexanone which are recycled to the first condensation reactor, and a third distillation column to separate an isomeric mixture of tricyclic ketones from the remainder of the organic phase;

i. passing said isomeric mixture of tricyclic ketones through a dehydrogenation catalyst in a fixed bed dehydrogenation reactor maintained at a temperature from 240° to 360° C. to produce a mixture of 2,6-diphenylphenol and partially dehydrogenated by-products; and j. recovering 2,6-diphenylphenol from said mixture.

2. A process as defined in claim 1 wherein, in step (b), said condensation product is removed from said reaction zone when the content of tricyclic ketone therein is from 30 to 45% by weight.

3. A process as defined in claim 1 wherein the condensation temperature is from 170° to 190°C.; the dehydrogenation temperature is from 300° to 350°C.; and the dehydrogenation catalyst is platinum or palladium deposited on a substrate.

4. A process as defined in claim 1 wherein said alkaline catalyst is sodium hydroxide.

5. A process as defined in claim 1 wherein said dehydrogenation catalyst is platinum deposited on an alumina substrate.

6. A process as defined in claim 1 wherein two condensation reactors in series are used in the reactor zone.

* * * * *